United States Patent
Schrader et al.

(10) Patent No.: US 7,171,966 B2
(45) Date of Patent: Feb. 6, 2007

(54) BREATHING MASK WITH A SUPERELASTIC SEAL

(75) Inventors: Cornelia Schrader, Lübeck (DE); Jörg-Uwe Meyer, Ratzeburg (DE); Götz Kullik, Lübeck (DE); Hans-Ullrich Hansmann, Barnitz (DE)

(73) Assignee: Drägerwerk Aktiengesellschaft (DE)

( * ) Notice: Subject to any disclaimer, the term of this patent is extended or adjusted under 35 U.S.C. 154(b) by 32 days.

(21) Appl. No.: 11/082,426

(22) Filed: Mar. 17, 2005

(65) Prior Publication Data
US 2005/0284477 A1    Dec. 29, 2005

(30) Foreign Application Priority Data
Jun. 23, 2004  (DE) .................... 10 2004 030 067

(51) Int. Cl.
*A62B 18/02*   (2006.01)
(52) U.S. Cl. ............... 128/205.25; 128/206.26; 128/206.27; 128/206.28; 128/206.24; 128/207.11; 128/207.13
(58) Field of Classification Search ........... 128/206.24, 128/206.26, 206.27, 207.11, 207.13, 206.28
See application file for complete search history.

(56) References Cited

U.S. PATENT DOCUMENTS

| 4,257,414 | A | * | 3/1981 | Gamm et al. ............... 602/72 |
| 4,770,169 | A | * | 9/1988 | Schmoegner et al. ........... 128/207.13 |
| 5,003,633 | A | * | 4/1991 | Itoh ........................ 2/9 |
| 5,094,236 | A | * | 3/1992 | Tayebi ................ 128/206.12 |
| 5,738,094 | A | * | 4/1998 | Hoftman ............... 128/206.26 |
| 6,016,805 | A | * | 1/2000 | Burns et al. .......... 128/206.24 |
| 6,712,072 | B1 | * | 3/2004 | Lang .................... 128/206.27 |
| 6,945,249 | B2 | * | 9/2005 | Griesbach et al. ..... 128/206.12 |

FOREIGN PATENT DOCUMENTS

WO    WO 99/43375    *    9/1999

* cited by examiner

*Primary Examiner*—Henry Bennett
*Assistant Examiner*—Nihir Patel
(74) *Attorney, Agent, or Firm*—McGlew & Tuttle, PC

(57) ABSTRACT

A breathing mask with a mask body, which has a seal at its edge, which said seal is in contact with the user's face, wherein at least part of the seal that is in contact with the user's face is elastically deformable with spring characteristics ranging from linear to progressive and at least part of the seal that is in contact with the user's face is elastically deformable with degressive spring characteristic.

13 Claims, 4 Drawing Sheets

BREATHING MASK WITH A SUPERELASTIC SEAL

CROSS REFERENCE TO RELATED APPLICATIONS

This application claims the benefit of priority under 35 U.S.C. § 119 of DE 10 2004 030 067.4 filed Jun. 23, 2004, the entire contents of which are incorporated herein by reference.

FIELD OF THE INVENTION

The present invention pertains to a breathing mask with a superelastic seal, which already brings about a sealing action when pressed onto the face with a weak pressure.

BACKGROUND OF THE INVENTION

Masks sealing in such a way may be used wherever the airways are to be protected from the undesired effect of various substances, which may be inhaled with the breathing air, or where breathing gases, to which medically indicated components are optionally added, are to be specifically introduced. This may be exemplified by breathing masks that are delivered with respirators in the broadest sense of the word.

These include, among other things, devices for patients who require respiratory support for various reasons, e.g., sleep apnea or COPD (chronic obstructive pulmonary disease). Such disorders of spontaneous breathing are frequently treated with CPAP respirators or similar devices. CPAP stands for continuous positive airway pressure.

A settable overpressure is made available here for the patient for supporting the respiration. The supply is frequently ensured with constant pressure over the entire breathing cycle via breathing mask. An overpressure prevails in the breathing mask in relation to the environment, which is set between a few mbar and up to 50 mbar depending on the therapy. To maintain this overpressure in the interior of the mask, the mask is usually sealed with a seal between the mask body and the user's face.

An expiration valve partially ensures that the expired air can escape into the environment when a sufficient pressure increase is generated in the interior of the mask by the expiration. At the same time, it ensures the scavenging of the mask with fresh breathing gases due to a continuously flowing volume flow.

A leak rate of a few L per minute can be tolerated during such applications, in which fresh gas scavenging takes place in the interior of the mask. By contrast, maximum sealing action is desirable for other critical applications.

The sealing action is achieved, especially in so-called half masks, by the mask body being limited circumferentially by a seal, which is pressed against the face of the user by pressing on the mask and thus ensures the desired sealing. The wearing comfort of such masks is determined essentially by the manner in which the force applied to press on the mask is transmitted as a pressing pressure via the seal onto the face in the area of the contact line between the mask and the face. The interior of the mask is sealed against the environment along this contact line. Each area of the contact line must be pressed sufficiently firmly against the user's face especially in case of applications that operate with an overpressure in the interior of the mask in order to counteract the tendency of the mask lifting off. However, due to their nature, conventional mask bodies are only conditionally suitable for uniform transmission of forces to irregularly shaped and changing surfaces over the contour of their own edge, a pressing force that may lead to needlessly high pressing pressures at some points of the face must be usually preset in order to guarantee the desired sealing action. A reduction of these strong pressing forces by generally reducing the pressing force, which would be able to be set, for example, by means of the strap of the mask, would be very likely to lead to leakages in other areas of the contact line as a consequence.

The seal on the contact line is frequently designed as a silicone lip or silicone tube embodying the function of a sealing strip. Besides the separation of the gases proper, the mask body, which can be adapted only conditionally, can be adapted, to a limited extent, to the contours of the face due to the elasticity of this sealing lip. A different deflection or deformation of the seal is necessary for this. Nevertheless, the problem that continues to be present is that zones with greatly different pressing pressures are formed if differences develop in the distance between the mask body and the contours of the face along the contact line. Each area with excessively low pressing pressure may lead to leakage. Any pressing pressure that is excessively low leads to a needless load for the corresponding zones of the face and may generate pressure points in these zones. The loss of wearing comfort associated herewith may, moreover, lead to acceptance problems during the use of the above-described masks.

Processes that are to bring about the highest possible flexibility of the sealing strip are known. These processes utilize the internal pressure of the interior space of the mask to support the pressing force by generating a degressive spring characteristic. However, this goal is reached only partially and is not applicable to all contact line geometries.

Thus, the problem that continues to be present is that the mask must be pressed onto the face with a markedly stronger force than would be necessary to compensate the force that could enable the mask to be lifted off as a function of the internal pressure in the mask and the area on which this internal pressure acts. The pressing force is usually built up by a tension of the straps and is transmitted to the mask body.

The higher the intended internal pressure and the more uniform the pressing pressure of the mask body on the face, the stronger must be the force with which the mask must be pressed on. If the internal pressure largely compensates the pressing pressure, the contact of the mask is not usually felt by the user to be unpleasant. However, sufficient sealing action cannot be expected in this state for the above-mentioned reasons in case of conventional masks because the local pressing pressure would already be below the internal pressure in the mask body over parts of the face on which the load is lower. The mask body would be lifted off from the face in such areas.

If, by contrast, the pressing force is markedly higher, the mask is frequently felt to be unpleasant, especially when an excessively nonuniform distribution of the pressing pressure leads to pressure peaks in individual areas of the seal.

SUMMARY OF THE INVENTION

The basic object of the present invention is to propose a breathing mask that is improved compared to the state of the art and that is characterized by a greater wearing comfort and prevents the development of peaks of the pressing pressure on the user's face, which are felt to be unpleasant.

The present invention is based on the fact that it is possible to let the pressing pressure act uniformly on the user's face and to reduce the dependence of the pressing pressure on the deflection of the seal corresponding to a conventional spring characteristic.

The present invention pertains to a breathing mask with a mask body, which has at its edge a seal that comes into contact with the user's face, wherein at least part of the seal that is in contact with the user's face is elastically deformable with a spring characteristic ranging from linear to progressive and at least part of the seal that is in contact with the user's face is elastically deformable with a degressive spring characteristic.

The so-called superelastic properties of support means, which are contained in the seals that are in direct contact with the user's face, are utilized for this purpose according to the present invention. The use of such seals leads to the pressing pressure of the breathing mask on the user's face to become constant. For example, nickel-titanium alloys possess superelastic properties and can manifest these properties in a temperature-dependent manner. In a temperature range in which such materials have a phase transition, they have the desired superelastic behavior. In response to weak forces at low deflection, they display elastic behavior, which is characterized by a linear spring characteristic, and they have an elastic behavior that is characterized by a degressive spring characteristic in response to stronger forces at greater deflection.

In other words, the seal at an edge of the mask body has one or more elastically deformable portion having a spring coefficient that is either constant or increases with deflection and with the use of the superelastic properties the seal has a portion that is elastically deformable with a spring coefficient that decreases with deflection. This is a seal portion exhibiting a spring force that increases linearly with an amount of deflection or increases more than an linearly with an amount of deflection and with a seal portion that increases less than linearly with an amount of deflection.

Above the transition range, i.e., beginning from about 40EC, they are, for example, in an austenite phase, and below the transition range, i.e., below about 20EC, they are in a martensite phase. The superelastic properties can be advantageously utilized within the transition range. Such alloys are also called shape memory alloys (SMAs). Their elastic properties differ from those of conventional steels and are also called quasi-elastic properties. The cause for the special mechanical properties of the aforementioned materials can be seen in shear within the metallic lattice planes. The material of which the superelastic support means are made consists essentially of a shape memory alloy.

Such materials frequently consist of nickel-titanium alloys of a slightly varying composition. Depending on the nickel content (50–60%), the titanium content (40–42%) and the contents of other metals, either the superelastic component or the shape memory component may predominate in different temperature ranges. In an advantageous embodiment, the seal is soft and flexible, is manufactured from an elastic material, for example, silicone, and has support means consisting of superelastic material.

It is likewise advantageous for designing the support means according to the present invention for the material of which the superelastic support means are made to consist essentially of an alloy that contains 50–60% of nickel and 40–42% of titanium. It is now advantageous for the seals according to the present invention that the human body temperature is in the transition range of such alloys, so that the superelastic properties described will appear in case of contact with the body.

It is especially advantageous if the superelastic support means comprise an array of longitudinally extending elements, which are curved in the shape of a banana and are arranged in parallel. The extension of the seal and the spring characteristic can thus be set by varying the radius of curvature.

In an especially advantageous embodiment, the individual longitudinally extending elements, which are curved in the shape of a banana and are arranged in parallel, have a tongue-shaped design and are connected with one another by a web structure, which fixes their position. An especially robust array of support means is thus obtained, especially when the superelastic support means are enclosed in the elastic material of which the seal consists.

The seal is advantageously fastened to a frame of the mask body.

The frame area partially assumes molding functions and absorbs the forces that develop due to the fastening of the mask to the head and it optionally receives inspiration and expiration connections. This frame is dimensionally stable, robust and hygienically satisfactory during use. If there are different distances between the edge of the mask body, i.e., for example, the frame, and the user's face, these distances can be bridged over nearly without increasing the pressing pressure by the extension of individual superelastic support means being adapted by superelastic deformation to the particular distance. This may take place, for example, by a change in the radius of curvature of the longitudinally extending elements, which are curved in the shape of a banana and are present in an advantageous embodiment of the present invention. As a result, a contour is formed, which is elastic in respect to weak forces and corresponds to the shape of the user's face. As a result, highly uniform distribution of the pressing pressure takes place on the user's face. The pressing pressure can be set at a relatively low value without having to fear leaks developing. Pressure points on the face are prevented from occurring.

The seal may advantageously be additionally plastically deformable or contain plastically deformable support means at least in some parts. A contour can thus be adapted to the shape of the face to support the elastic part of the seal by briefly pressing on more strongly due to plastic deformation of the plastic support means.

It is especially advantageous if the mask body can be additionally adapted to the shape of the face, in which case plastic adaptability offers additional advantages.

It is especially advantageous if the adaptation to the shape of the face can be performed by a moldable frame arranged in the vicinity of the edge of the mask body. Such a frame likewise stabilizes the shape of the edge of the mask body. It assumes the form-stabilizing function according to the contours of the user's face and is used to absorb the forces that are due to the internal pressure, the fastening on the head and optionally the mounting of the inspiration and expiration connections. This frame is sufficiently dimensionally stable, robust and hygienically satisfactory in use. Nevertheless, it makes possible the plastic deformation of the frame and consequently of the mask body for adaptation to the face of the user of the breathing mask by being pressed strongly onto the face or by another force action. Combined with a seal according to the present invention, which can be arranged on such a frame, especially good adaptability to the shape of the user's face is achieved. Rough adjustment may be performed by adapting the shape of the frame and a fine adjustment by adapting the shape of the superelastic and optionally plastic support means. The elastic part of the seal brings about the sealing of the interior space of the mask against the environment when the mask body is pressed on, and nearly the same pressing pressure will prevail in the entire contact area between the mask body and the face. Pressure points are thus prevented from occurring with certainty.

Especially comfortable is an embodiment of a seal according to the present invention when the superelastic support means are connected with the frame and are surrounded by an envelope, which can the connected with the frame and forms the seal. Elements that come into contact with the user's skin can thus be replaced or cleaned in a simple manner.

The present invention will be explained in greater detail below on the basis of exemplary embodiments shown in the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
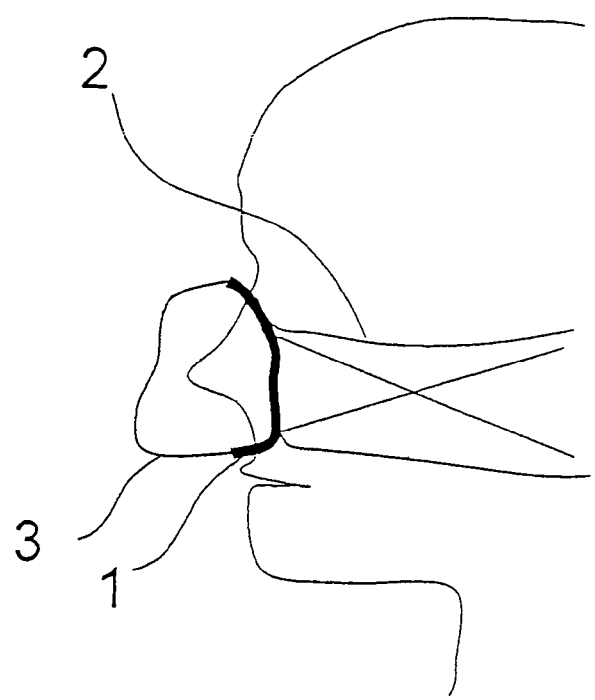
FIG. 1 is a schematic side view of a nasal CPAP mask according to the invention.
Figure 2:
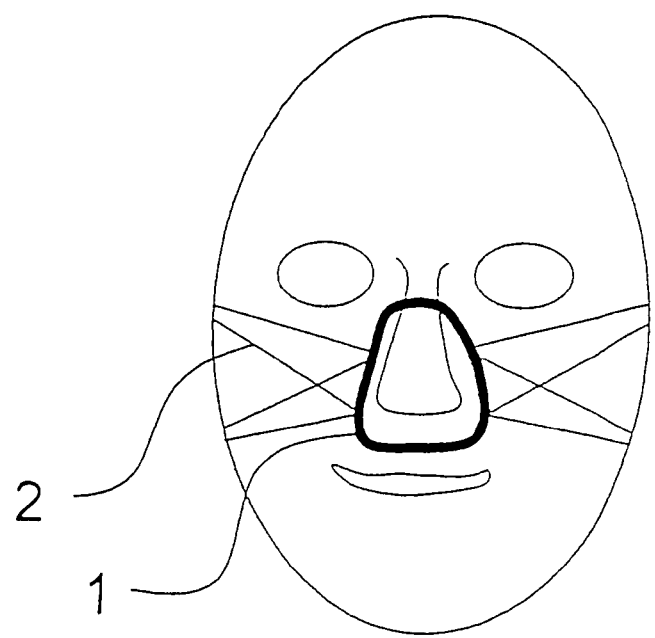
FIG. 2 is a schematic front view of a nasal CPAP mask.

Referring to the drawings in particular, in the first embodiment, FIGS. 1 and 2 show two views of a nasal CPAP mask. It is equipped with a partially superelastic seal 1. A strap 2 is used as a holding device for fixing the mask on the head and generates the necessary tensile force to counteract the overpressure in the interior of the mask body 3.

Figure 3:
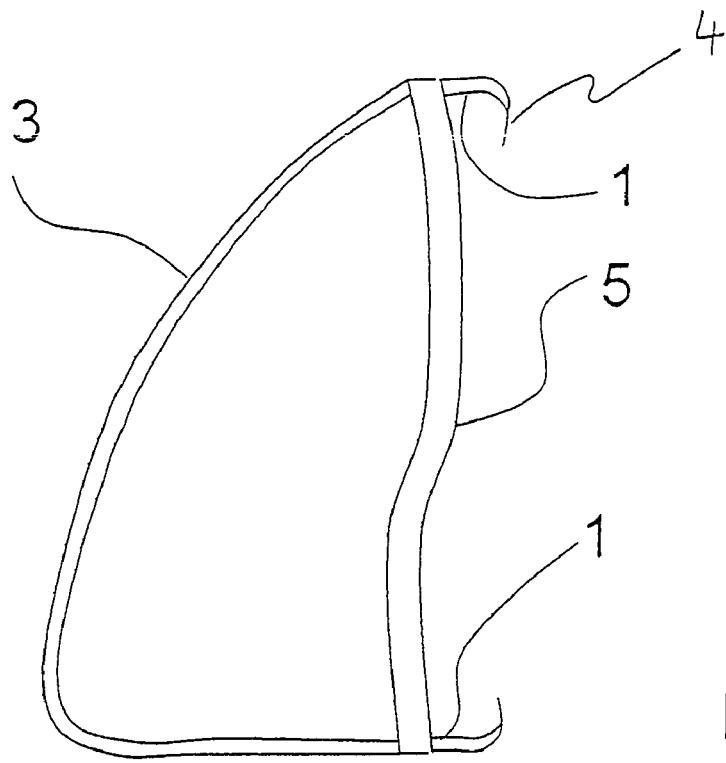
FIG. 3 is a schematic side view of a nasal CPAP mask with the sealing lip shown explicitly.

FIG. 3 shows a similar mask, whose mask body is equipped with a circumferential seal 1 in the form of a silicone lip, part of which can be folded over such that it acts as a contact surface 4 for the face of the user. The silicone lip 1 is fastened to a moldable frame 5, by which adaptation of the shape to the shape of the face can be performed. The frame 5 forms at the same time the closure of the mask body 3.

Figure 4:
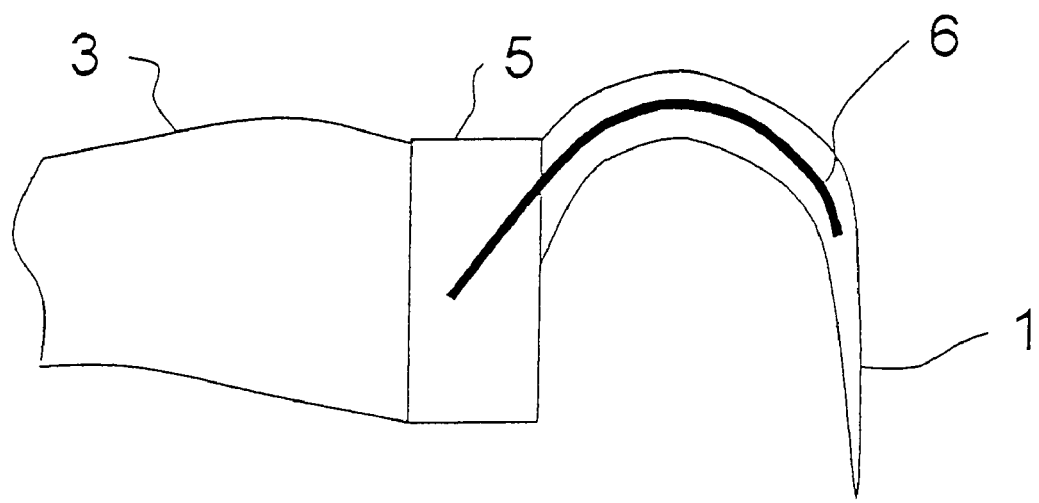
FIG. 4 is a partially cutaway view of the mask, showing a seal designed according to the present invention with superelastic support means.

FIG. 4 shows a view of a seal 1 designed according to the present invention with superelastic support means 6, which is fastened to the frame 5, which limits the mask body 3. Support means 6 made of a superelastic NiTi alloy are cast as an elastic support into a very thin, highly flexible sealing lip made of silicone. As an alternative, such support means may be extrusion-coated or buttoned into an envelope in a reusable manner. In any case, the elastic properties of the alloy and the properties of the silicone are advantageously combined with one another in such a sealing lip. The superelastic support means 6 are designed in this exemplary embodiment as longitudinally extending elements, which are curved in the shape of a banana and are arranged in parallel.

Their radius of curvature of the longitudinally extending superelastic support elements 6, determined by the distance between the frame 5 of the mask body and the part of the seal 1 that acts exclusively elastically and is brought into contact with the user's face affects the spring characteristics of the seal pressed on. By changing the radius of curvature, this spring characteristic can be varied from progressive to degressive.

Figure 5:
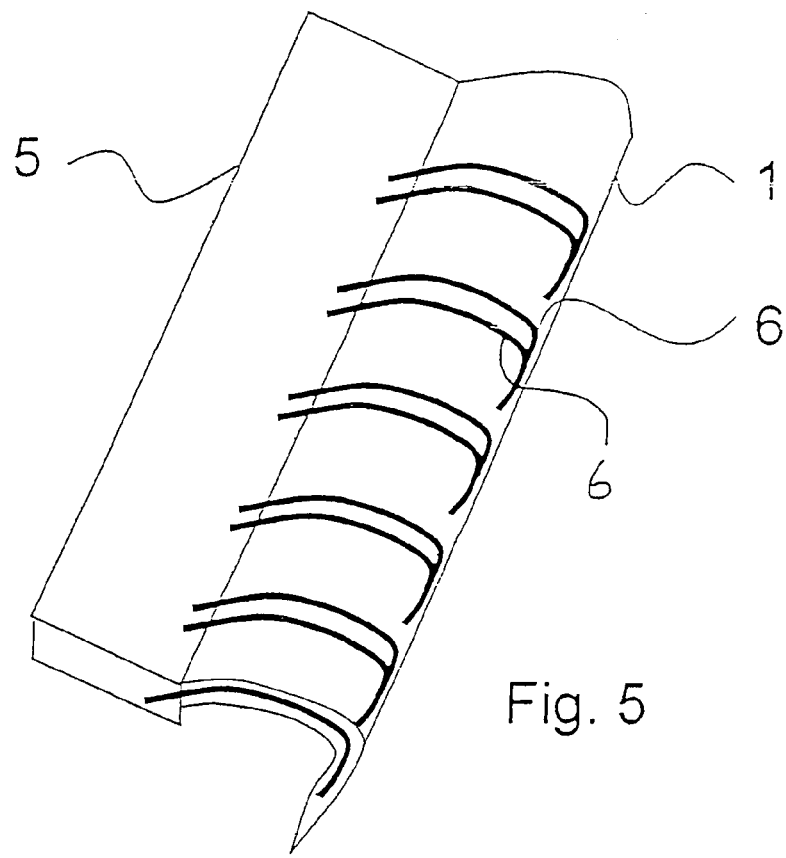
FIG. 5 is a view of an advantageous arrangement of superelastic support means in a seal according to the present invention.

FIG. 5 shows an advantageous arrangement of superelastic support means 6 in a seal 1 according to the present invention, which is arranged on the frame 5 of a mask body. It becomes clear that the superelastic support means 6 comprise an array of longitudinally extending elements, which are curved in the shape of a banana and are arranged in parallel. It is especially advantageous if individual support elements 6' display plastic behavior. As a result, it is possible to achieve an additional presettability of the seal to the shape to be sealed. The elastic part of the seal is thus always positioned at a short and relatively uniform distance from the face and can be partly supported against an initially elastic contour, which is, however, produced by plastic deformation when the mask is pressed on. As a result, the pressing pressure will be distributed uniformly on the user's face. The pressing pressure may be set at a relatively low value without having to fear the development of leaks. Pressure points on the face are prevented from occurring. By pressing on more strongly, the contour can again be adapted to the shape of the face by the repeated plastic deformation of the plastic support means 6' for partially supporting the elastic part of the seal.

Figure 6:
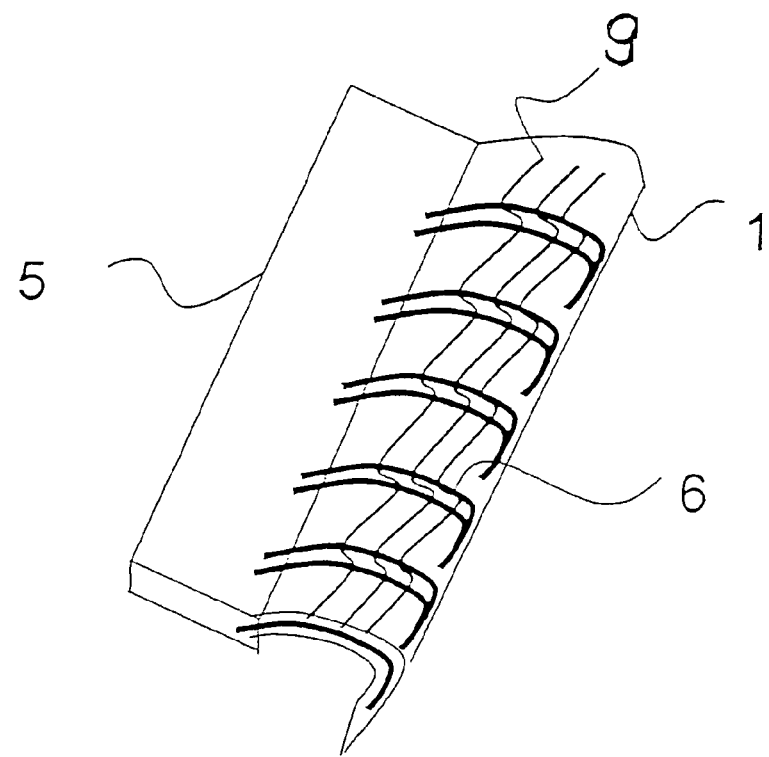
FIG. 6 is another view of an advantageous arrangement of superelastic support means in a seal according to the present invention.

FIG. 6 shows another view of an advantageous array of superelastic support elements 6 in a seal 1 according to the present invention, in which the individual longitudinally extending elements, which are curved in the shape of a banana and are arranged in parallel, have a tongue-shaped design and are connected with one another by a web structure 9, which fixes their position. Especially in case of the design as superelastic flexible tongues, the useful properties of the material of the support means can be advantageously combined with the properties of the elastic material surrounding them.

Figure 7:
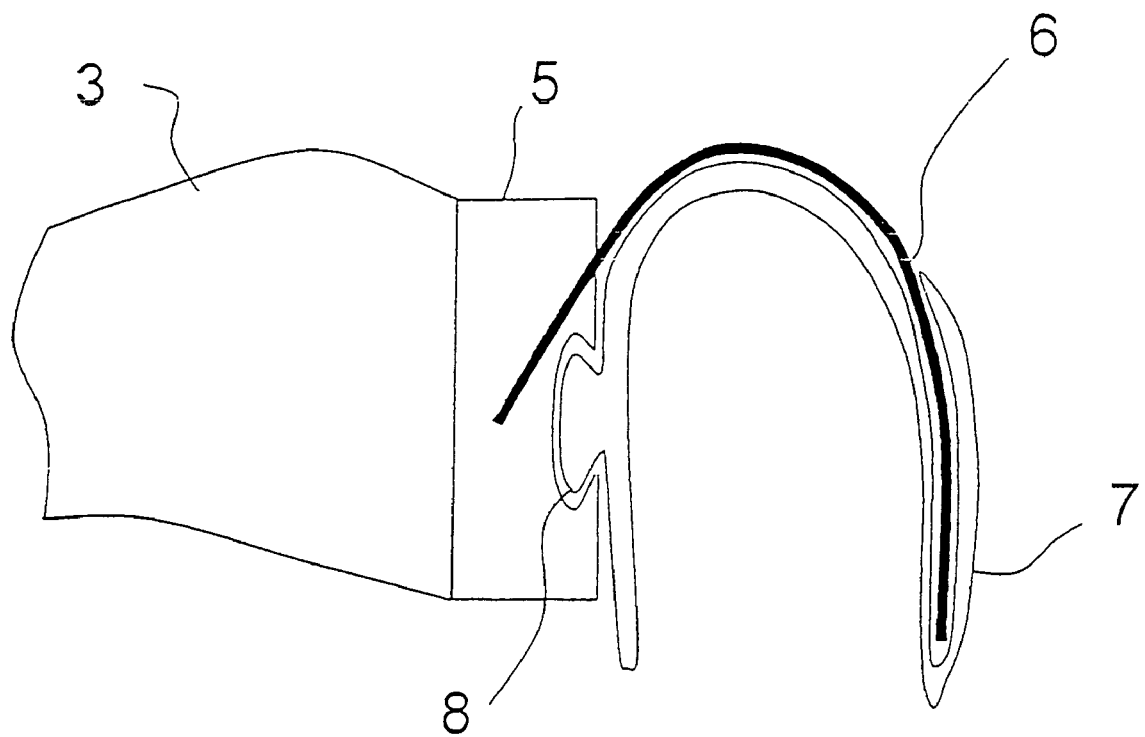
FIG. 7 is a view of a seal designed according to the present invention as an envelope that can be connected, with superelastic support means.

FIG. 7 shows a view of a seal designed according to the present invention as an envelope 7 that can be connected with superelastic support elements 6. The envelope 7 that can be connected consists of silicone and partially winds around the superelastic support means 6, which are fastened to the frame 5 of the mask body. As a result, it is ensured that the superelastic support elements 6 will not come into contact with the mask user's face. The connection of the envelope 7 that can be connected is established by means of a fastening element 8, by which a connection is established with the frame 5. The design of a seal according to the present invention as an envelope that can be connected makes it possible to replace or clean the components of the seal that come into contact with the user's face in a simple manner.

While specific embodiments of the invention have been shown and described in detail to illustrate the application of the principles of the invention, it will be understood that the invention may be embodied otherwise without departing from such principles.

What is claimed is:

1. A breathing mask, comprising:
a mask body having a front and a rear edge;
a seal at an edge of said mask body, at least part of the seal that is in contact with the user's face is elastically deformable with a spring characteristic ranging from linear to progressive, and at least part of the seal that is in contact with the user's face is elastically deformable with a degressive spring characteristic, wherein said seal comprises an elastic material and a superelastic support means made of a superelastic material wherein said superelastic support means comprises an array of longitudinally extending elements, which are curved over a rearward extent and including a portion adjacent to said rear edge that extends rearwardly and radially outwardly curving to a portion spaced away from said rear edge that extends rearwardly and radially inwardly and wherein said longitudinally extending elements are arranged in parallel.

2. A breathing mask in accordance with claim 1, wherein part of said seal is plastically deformable.

3. A breathing mask in accordance with claim 1, wherein said superelastic support means comprises a material consisting essentially of a shape memory alloy.

4. A breathing mask in accordance with claim 1, wherein said superelastic support means comprises a material consisting essentially of an alloy that contains 50–60% of nickel and 40–42% of titanium.

5. A breathing mask in accordance with claim 1, wherein said, longitudinally extending elements, are connected with one another by a web structure which fixes their position.

6. A breathing mask in accordance with claim 1, wherein said superelastic support means is enclosed in said elastic material.

7. A breathing mask in accordance with claim 1, wherein the mask body can be adapted to the shape of the face.

8. A breathing mask in accordance with claim 7, further comprising a moldable frame arranged in the vicinity of the rear edge of said mask body wherein the adaptation to the shape of the mask can be performed by means of said moldable frame.

9. A breathing mask in accordance with claim 1, wherein a moldable frame is associated with the rear edge of said mask body, said superelastic support elements being connected with said frame and being surrounded by an envelope of said elastic material, said envelope being connected with said frame to form said seal.

10. A breathing mask in accordance with claim 1, wherein said seal includes a portion consisting of silicone.

11. A breathing mask in accordance with claim 1, wherein said superelastic material of said support means possesses superelastic properties at least at body temperature.

12. A breathing mask comprising:
a mask body; and
a seal at an edge of said mask body, said seal being elastically deformable with a portion having a spring coefficient that is either constant or increases with deflection and with a portion that is elastically deformable with a spring coefficient that decreases with deflection, wherein said seal comprises an elastic material with a support superelastic means made of a superelastic material consisting essentially of an alloy that contains 50–60% of nickel and 40–60% of titanium.

13. A breathing mask comprising:
a mask body with a frame defining a mask body shape, the mask body having a front and a rear edge; and
a seal at an edge of said mask body, said seal comprising a superelastic material support part with an end fixed to said frame and extending rearwardly from said frame and having a curved shape over a rearward extent and including a portion adjacent to said rear edge that extends rearwardly and radially outwardly curving to a portion spaced away from said rear edge that extends rearwardly and radially inwardly and an elastic material part at least partially covering said support part and forming a sealing lip, said seal having at least a portion being elastically deformable with a spring characteristic ranging from linear to progressive, and having at least another portion that is elastically deformable with a degressive spring characteristic.

* * * * *